(12) United States Patent
Takayama et al.

(10) Patent No.: US 7,956,072 B2
(45) Date of Patent: Jun. 7, 2011

(54) AGENT FOR REPAIRING CORNEAL SENSITIVITY CONTAINING AMIDE COMPOUND

(75) Inventors: Yoshiko Takayama, Kobe (JP); Yoshikuni Nakamura, Kobe (JP); Jun Inoue, Kobe (JP); Mitsuyoshi Azuma, Nishinomiya (JP)

(73) Assignees: Senju Pharmaceutical Co., Ltd., Osaka (JP); Mitsubishi Tanabe Pharma Corporation, Osaka (JP)

( * ) Notice: Subject to any disclaimer, the term of this patent is extended or adjusted under 35 U.S.C. 154(b) by 284 days.

(21) Appl. No.: 12/289,748

(22) Filed: Nov. 3, 2008

(65) Prior Publication Data
US 2009/0118322 A1    May 7, 2009

Related U.S. Application Data

(62) Division of application No. 10/557,415, filed as application No. PCT/JP2005/010624 on Jun. 3, 2005, now Pat. No. 7,485,654.

(30) Foreign Application Priority Data

Jun. 3, 2004   (JP) .................. 2004-166445

(51) Int. Cl.
 A61K 31/445   (2006.01)
 A61K 31/44    (2006.01)
(52) U.S. Cl. ........ 514/352; 514/241; 514/243; 514/245; 514/256
(58) Field of Classification Search ............ 514/47, 514/50, 86, 300, 303, 326, 352
See application file for complete search history.

(56) References Cited

U.S. PATENT DOCUMENTS

| | | | |
|---|---|---|---|
| 5,958,944 A | 9/1999 | Arita et al. | |
| 6,218,410 B1 | 4/2001 | Uehata et al. | |
| 6,277,855 B1 | 8/2001 | Yerxa | |
| 6,649,625 B2 * | 11/2003 | Azuma et al. | 514/303 |
| 6,673,812 B1 | 1/2004 | Azuma et al. | |
| 7,109,208 B2 | 9/2006 | Takayama et al. | |
| 7,485,654 B2 | 2/2009 | Takayama et al. | |
| 2003/0125351 A1 | 7/2003 | Azuma et al. | |
| 2004/0106646 A1 | 6/2004 | Takayama et al. | |
| 2004/0162315 A1 | 8/2004 | Hellberg et al. | |
| 2006/0234922 A1 | 10/2006 | Takayama et al. | |

FOREIGN PATENT DOCUMENTS

| | | |
|---|---|---|
| EP | 1 034 793 | 9/2000 |
| EP | 1 566 184 | 8/2005 |
| WO | 2004/039403 | 5/2004 |

OTHER PUBLICATIONS

Office Action issued in CN 200580000389.9 (with English translation).
T. U. Linna et al., "Recovery of Corneal Nerve Morphology Following Laser in situ Keratomileusis", Exp. Eye Res., vol. 66, pp. 755-763, 1998.
T. U. Linna et al., "Effect of Myopic LASIK on Corneal Sensitivity and Morphology of Subbasal Nerves", Investigative Ophthalmology & Visual Science, vol. 41, No. 2, pp. 393-397, Feb. 2000.
R. T. Ang et al., "Dry eye after refractive surgery", Current Opinion in Ophthalmology, vol. 12, pp. 318-322 2001.
P. H. Ozdinler et al., "Regulation of Neurotrophin-Induced Axonal Responses via Rho GTPases", The Journal of Comparative Neurology, vol. 438, pp. 377-387, 2001.
M. Negishi et al., "Rho Family GTPases as Key Regulators for Neuronal Network Formation", J. Biochem., vol. 132, No. 2, pp. 157-166, 2002.
J. Horwath-Winter et al.,"Early changes in corneal sensation, ocular surface integrity, and tear-film function after laser-assisted subepithelial keratectomy", J. Cataract Refract Surg., vol. 30, pp. 2316-2321, Nov. 2004.
Y. Chan et al., "Specificity a Neuronotrophic Factor from Rabbit Corneal Epithelial Cultures", Exp. Eye. Res., vol. 41, pp. 687-699, 1985.
M. C. Arbelaez, "Nidek MK 2000 Microkeratome Clinical Evaluation", Journal of Refractive Surgery, vol. 18, pp. S357-S360, May/Jun. 2002.
Saini Jagjit S, Mittal Sangeet, Graded corneal sensitivity for screening of diabetic retinopathy, Indian J. Ophthalmology, 44(4), 219-223, 1996.

* cited by examiner

*Primary Examiner* — Michael G Hartley
*Assistant Examiner* — Jagadishwar Samala
(74) *Attorney, Agent, or Firm* — Wenderoth, Lind & Ponack, L.L.P.

(57) ABSTRACT

The amide compound of the formula (I) [each symbol is as defined in the description] has a promoting action on neuritogenesis of trigeminal nerve cells, and the compound is useful as a corneal neuritogenesis promoter, an agent for recovering corneal sensitivity by promotion of corneal neuritogenesis, and an agent for treating dry eye.

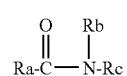

(a)

6 Claims, 2 Drawing Sheets

AGENT FOR REPAIRING CORNEAL SENSITIVITY CONTAINING AMIDE COMPOUND

This is a divisional of Ser. No. 10/557,415, filed Dec. 12, 2005 now U.S. Pat. No. 7,485,654, which is a U.S. national stage of International Application No. PCT/JP2005/010624, filed Jun. 3, 2005.

TECHNICAL FIELD

The present invention relates to an agent for promoting corneal neuritogenesis, an agent for repairing corneal sensitivity based on the promotion of corneal neuritogenesis and therapeutic agent for dry eye.

BACKGROUND ART

Since corneal nerve is severed by corneal surgeries such as Laser photorefractive keratectomy (PRK), Laser-Assisted-In-Situ Keratomileusis (LASIK), keratoplasty and the like, the functional reduction of corneal sensitivity is said to occur for generally about 3 weeks to one year. For example, it has been reported that the corneal nerve is apparently severed after LASIK (Tuuli U. Linna et al., Experimental Eye Research 66: 755-763, 1998), and the corneal sensitivity decreases in a corneal region where, after LASIK, neurogram is not observed or the nerve bundle is too short to create connection (Tuuli U. Linna et al., Investigative Ophthalmology & Visual Sciences, 41: 393-397, 2000).

It has been demonstrated that the corneal hyposensitivity after PRK and LASIK causes lower lacrimal gland response and decreased lacrimal fluid (Ang, Robert T. et al., Current Opinion in Ophthalmology 12: 318-322, 2001). As a result of the hypofunction of corneal sensitivity, patients after a corneal surgery blink less number of times, problematically showing the symptoms of dry eye. In the patients with dry eye, lacrimal hypofunction gives rise to corneal hyposensitivity, which, upon combination with further lacrimal hypofunction, problematically aggravates the condition of corneal surface.

At present, however, recovery of corneal hyposensitivity after corneal surgery is left to spontaneous recovery, and in the treatment of dry eye, no active treatment is provided to recover corneal sensitivity. Moreover, while corneal hyposensitivity is caused by the diseases accompanying corneal neurodegeneration, such as neuroparalytic keratopathy, corneal ulcer, diabetic keratopathy and the like, no appropriate cure is available at present.

Rho-kinase is a serine/threonine kinase activated along with the activation of Rho, which is a low molecular weight G protein, and is known to control diversified physiological functions such as smooth muscle contraction, neurite retraction and the like, by phosphorylation of various substrates. A compound having an inhibitory activity of such Rho-kinase is expected to provide various pharmaceutical uses and there has been suggested use as a therapeutic drug for, for example, hypertension, angina pectoris, cerebrovascular contraction, asthma, peripheral circulation disorder, arteriosclerosis, osteoporosis, retinopathy and the like, as well as an anti-cancer drug, an anti-inflammatory drug, an immunosuppressant and the like (e.g., WO98/06433). In addition, Rho-kinase inhibitors are known to be useful for the improvement of visual function disorder, since they have an axon extension action of retinal ganglion cells (WO02/083175). Due to this action, Rho-kinase inhibitors are considered to promote regeneration of optic nerve cells and be useful for the treatment of visual function disorders associated with various eye diseases caused by damage, defect, degeneration and the like of retina and optic nerve. However, this reference does not at all describe effects of Rho-kinase inhibitor on corneal diseases such as corneal hyposensitivity and the like.

The corneal sensitivity is controlled by trigeminal nerve (corneal nerve), which is a sensory nerve distributed in the cornea. As regards the relationship between Rho and the trigeminal nerve, it has been reported that, in a rat trigeminal nerve tissue culture (trigeminal tract in whole mount cultures) system, neurotrophin (e.g., nerve growth factor (NGF) etc.)—induced extension of nerve axon is inhibited by a Rho activator (lysophosphatidic acid), and facilitated by introduction of dominant negative Rho into a cell (Ozdinler, P. Hande et al., The Journal of Comparative Neurology, 438:377-387, 2001). However, there is a description that whether Rho is effective for trigeminal nerve axon extension in the absence of neurotrophin is unknown (Ozdinler, P. Hande et al., The Journal of Comparative Neurology, 438:377-387, 2001), and the effect of a Rho-kinase inhibitor on the trigeminal nerve has not been elucidated.

There are references teaching that compounds that promote neuron regeneration or neurite outgrowth are usable for the treatment of corneal nerve damage after surgery such as LASIK and the like, and as examples of such compounds, Neotrofin, which is a neurotrophic factor stimulator, and the like are shown (WO03/020281). However, WO03/020281 does not at all describe Rho-kinase or an inhibitor thereof, or any description suggestive thereof.

DISCLOSURE OF THE INVENTION

The present invention aims at providing a pharmaceutical agent for effectively recovering hypofunction of corneal sensitivity after corneal surgery such as laser photorefractive keratectomy (PRK), laser keratomileusis (LASIK), LASEK; Laser epithelial keratomileusis; Jutta Horwath-Winter et al. J Cataract Refract Surg 30: 2316-2321, 2004), keratoplasty and the like, and corneal neurodegenerative diseases such as diabetic keratopathy and the like, hypofunction of corneal sensitivity associated with dry eye, and a pharmaceutical agent to effectively recover dry eye in patients having corneal hyposensitivity.

The present inventors have studied in an attempt to provide a novel pharmaceutical agent that improves recovery of corneal sensitivity after corneal surgery and dry eye associated with corneal hyposensitivity, and found that an amide compound having a particular structure acts on the trigeminal nerve and effectively promotes neuritogenesis of the trigeminal nerve cells. Based on this finding, moreover, they have found that the amide compound is useful as a pharmaceutical agent for promotion of corneal neuritogenesis, recovery of corneal sensitivity and treatment of dry eye, which resulted in the completion of the present invention.

Accordingly, the present invention relates to
(1) an agent for promoting corneal neuritogenesis, which comprises an amide compound represented by the formula (I):

wherein
Ra is a formula:

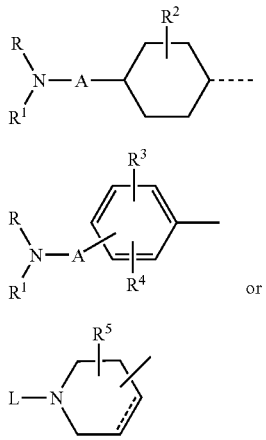

wherein
in the formulas (a) and (b),
R is hydrogen, alkyl, or cycloalkyl, cycloalkylalkyl, phenyl or aralkyl, each optionally having substituent(s) on the ring, or a formula:

(d)

wherein
$R^6$ is hydrogen, alkyl or a formula: —$NR^8R^9$
wherein $R^8$ and $R^9$ are the same or different and each is hydrogen, alkyl, aralkyl or phenyl, and
$R^7$ is hydrogen, alkyl, aralkyl, phenyl, nitro or cyano,
or $R^6$ and $R^7$ in combination form a heterocyclic group further optionally containing, in the ring, an oxygen atom, a sulfur atom, or a nitrogen atom optionally having a substituent,
$R^1$ is hydrogen, alkyl, or cycloalkyl, cycloalkylalkyl, phenyl or aralkyl, each optionally having substituent(s) on the ring,
or R and $R^1$ in combination form, together with the adjacent nitrogen atom, a heterocyclic group further optionally containing, in the ring, an oxygen atom, a sulfur atom, or a nitrogen atom optionally having a substituent,
$R^2$ is hydrogen or alkyl,
$R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or di-alkylcarbamoyl or azido, and
A is a formula:

(e)

—$(CH_2)_l(C)_m(CH_2)_n$— wherein
$R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ in combination form cycloalkyl, and l, m, n are each 0 or an integer of 1-3, and
in the formula (c),
L is hydrogen, alkyl, aminoalkyl, mono- or di-alkylaminoalkyl, tetrahydrofurfuryl, carbamoylalkyl, phthalimidoalkyl, amidino, or a formula:

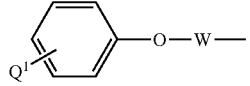

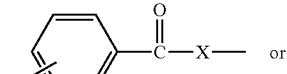

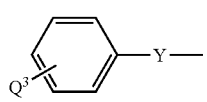

wherein
B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl,
$Q^1$ is hydrogen, halogen, a hydroxyl group, aralkyloxy or thienylmethyl,
W is alkylene,
$Q^2$ is hydrogen, halogen, a hydroxyl group or aralkyloxy,
X is alkylene,
$Q^3$ is hydrogen, halogen, a hydroxyl group, alkoxy, nitro, amino, 2,3-dihydrofuryl or 5-methyl-3-oxo-2,3,4,5-tetrahydropyridazin-6-yl, and
Y is a single bond, alkylene or alkenylene,
a bond shown by a broken line and a solid line in the formula (c) is a single bond or a double bond, and
$R^5$ is hydrogen, a hydroxyl group, alkoxy, alkoxycarbonyloxy, alkanoyloxy or aralkyloxycarbonyloxy,
Rb is hydrogen, alkyl, aralkyl, aminoalkyl or mono- or di-alkylaminoalkyl, and
Rc is a nitrogen-containing heterocycle optionally having substituent(s),
an isomer thereof and/or a pharmaceutically acceptable acid addition salt thereof, or a prodrug thereof;
(2) the agent of the above-mentioned (1), wherein Ra is a formula:

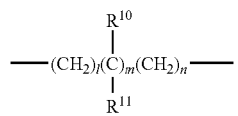

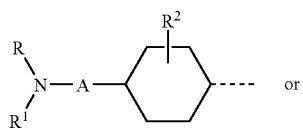

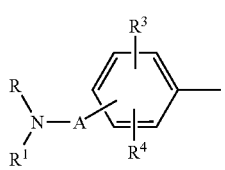

wherein each symbol is as defined in the above-mentioned (1);
(3) the agent of the above-mentioned (1), wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride;

(4) an agent for recovering corneal sensitivity, which comprises an amide compound represented by the above-mentioned formula (I), an isomer thereof and/or a pharmaceutically acceptable acid addition salt thereof, or a prodrug thereof;

(5) the agent of the above-mentioned (4), wherein Ra is a formula:

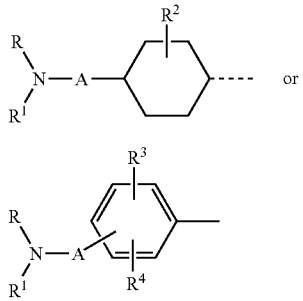

wherein each symbol is as defined in the above-mentioned (1);

(6) the agent of the above-mentioned (4), wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride;

(7) an agent for treating dry eye comprising an amide compound represented by the above-mentioned formula (I), an isomer thereof and/or a pharmaceutically acceptable acid addition salt thereof, or a prodrug thereof;

(8) the agent of the above-mentioned (7), wherein Ra is a formula:

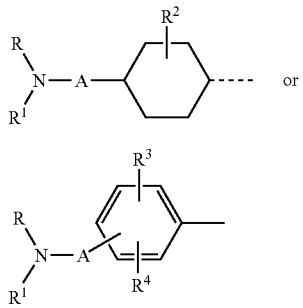

wherein each symbol is as defined in the above-mentioned (1);

(9) the agent of the above-mentioned (7), wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride;

(10) use of an amide compound represented by the above-mentioned formula (I), an isomer thereof and/or a pharmaceutically acceptable acid addition salt thereof, or a prodrug thereof, for the production of a pharmaceutical agent for promoting corneal neuritogenesis;

(11) use of the above-mentioned (10), wherein Ra is a formula:

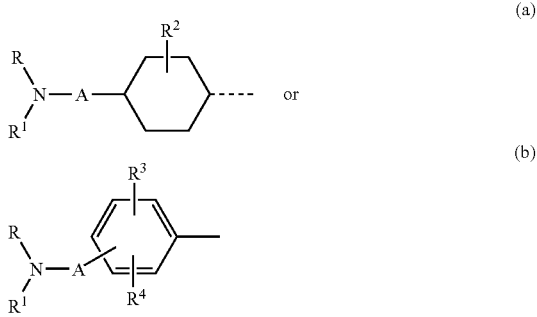

wherein each symbol is as defined in the above-mentioned (1);

(12) use of the above-mentioned (10), wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride;

(13) use of an amide compound represented by the above-mentioned formula (I), an isomer thereof and/or a pharmaceutically acceptable acid addition salt thereof, or a prodrug thereof, for the production of a pharmaceutical agent for recovering corneal sensitivity;

(14) the use of the above-mentioned (13), wherein Ra is a formula:

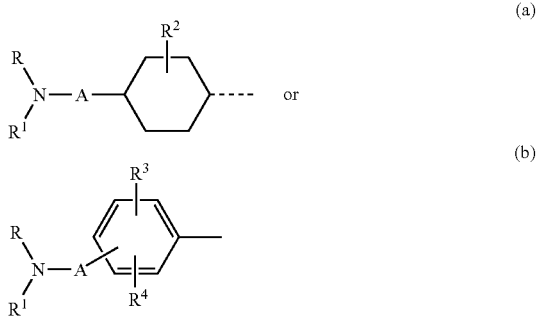

wherein each symbol is as defined in the above-mentioned (1);

(15) the use of the above-mentioned (13), wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride;

(16) use of an amide compound represented by the above-mentioned formula (I), an isomer thereof and/or a pharmaceutically acceptable acid addition salt thereof, or a prodrug thereof, for the production of a pharmaceutical agent for treating dry eye;

(17) the use of the above-mentioned (16), wherein Ra is a formula:

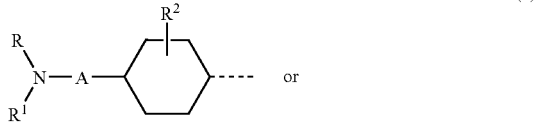

-continued (b)
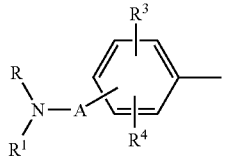

wherein each symbol is as defined in the above-mentioned (1);

(18) the use of the above-mentioned (16), wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride;

(19) a method for promoting corneal neuritogenesis, which comprises administering an effective amount of an amide compound represented by the above-mentioned formula (I), an isomer thereof and/or a pharmaceutically acceptable acid addition salt thereof, or a prodrug thereof, to a subject in need of promotion of corneal neuritogenesis;

(20) the method of the above-mentioned (19), wherein Ra is a formula:

(a)
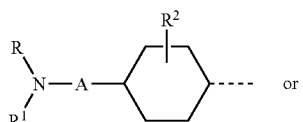

(b)
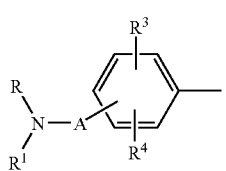

wherein each symbol is as defined in the above-mentioned (1);

(21) the method of the above-mentioned (19), wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride;

(22) a method of recovering corneal sensitivity, which comprises administering an effective amount of an amide compound represented by the above-mentioned formula (I), an isomer thereof and/or a pharmaceutically acceptable acid addition salt thereof, or a prodrug thereof, to a subject in need of recovery of corneal sensitivity;

(23) the method of the above-mentioned (22), wherein Ra is a formula:

(a)
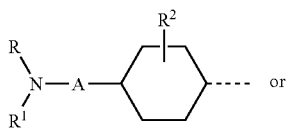

-continued (b)
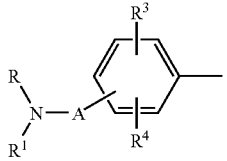

wherein each symbol is as defined in the above-mentioned (1);

(24) the method the above-mentioned (22), wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride;

(25) a method for treating dry eye, which comprises administering an effective amount of an amide compound represented by the above-mentioned formula (I), an isomer thereof and/or a pharmaceutically acceptable acid addition salt thereof, or a prodrug thereof, to a subject in need of treatment of dry eye;

(26) the method of the above-mentioned (25), wherein Ra is a formula:

(a)
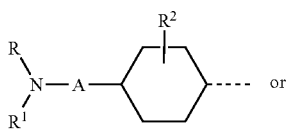

(b)
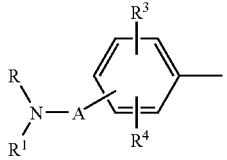

wherein each symbol is as defined in the above-mentioned (1);

(27) the method of the above-mentioned (25), wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride;

(28) a commercial package comprising a pharmaceutical agent comprising an amide compound represented by the above-mentioned formula (I), an isomer thereof and/or a pharmaceutically acceptable acid addition salt thereof, or prodrug thereof, and a written matter associated therewith, the written matter stating that the pharmaceutical agent can or should be used for promoting corneal neuritogenesis, recovering corneal sensitivity, or treating dry eye.

In the present description, an agent for promoting corneal neuritogenesis, an agent for recovering corneal sensitivity, and an agent for treating dry eye, each comprising the amide compound represented by the formula (I), are also to be collectively referred to as "the pharmaceutical agent of the present invention".

DETAILED DESCRIPTION OF THE INVENTION

Figure 1:
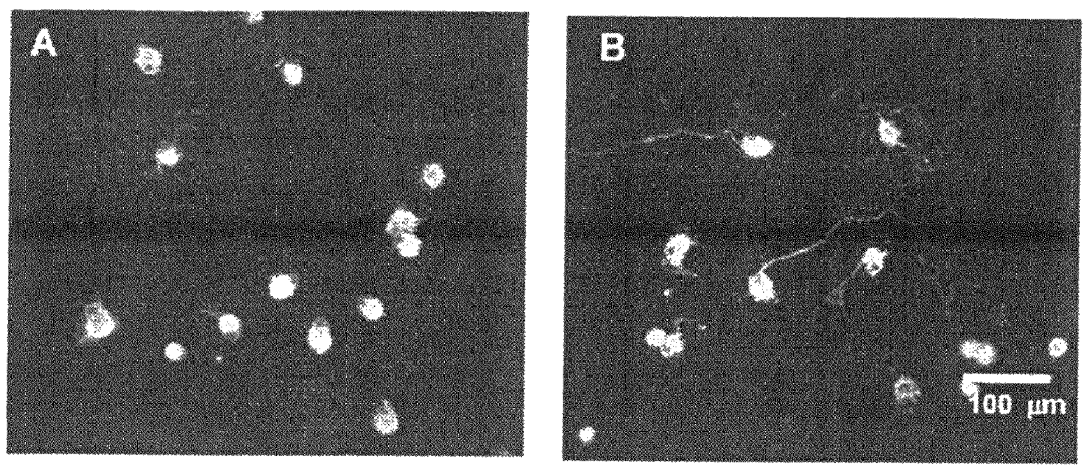
FIG. 1 is a fluorescence microscope image of cultured rabbit trigeminal nerve cells in Experimental Example 1, wherein A is a fluorescence microscope image of the cell cultured in a culture medium free of compound 1, and B is a fluorescence microscope image of the cell cultured in a culture medium supplemented with compound 1.

In the present description, the "corneal nerve" refers to annular plexus formed in the surrounding cornea, stroma plexus distributed reticulately in corneal stroma, sub-epithelial plexus formed immediately below Bowman's membrane, and basal cell plexus and nerve fiber formed immediately after penetrating Bowman's membrane, under the control of trigeminal nerve that is a sensory neuron. The "neurite" refers to a protrusion (dendrite and axon) from the cell body of neuron (nerve cell), and "genesis" refers to an outgrowth and/or extension of the aforementioned neurite from the cell body. It is clear to those of ordinary skill in the art what level of neuritogenesis is regarded as promotion. The level of neuritogenesis can be confirmed by, for example, fluorescent staining the nerve cell and observing the cell shape with a fluorescence microscope. In addition, the images observed with a fluorescence microscope may be analyzed using an image analysis software. Moreover, using an antibody that recognizes a substance constituting nerve cell body and neurite, such as neurofilament, and a reagent that makes it develop color, the amount of the neurofilament may be determined by measuring the absorbance and used as an index of the neuritogenesis.

In the present description, each symbol in the formula (I) is defined as follows.

The alkyl for R or $R^1$ is linear or branched chain alkyl having 1 to 10 carbon atoms, which is exemplified by methyl, ethyl, propyl, isopropyl, butyl, isobutyl, secondary butyl, tertiary butyl, pentyl, hexyl, heptyl, octyl, nonyl, decyl and the like, with preference given to alkyl having 1 to 4 carbon atoms.

The cycloalkyl for R or $R^1$ is cycloalkyl having 3 to 7 carbon atoms, such as cyclopropyl, cyclobutyl, cyclopentyl, cyclohexyl, cycloheptyl and the like.

The cycloalkylalkyl for R or $R^1$ is cycloalkylalkyl wherein the cycloalkyl moiety is the aforementioned cycloalkyl having 3 to 7 carbon atoms, and the alkyl moiety is linear or branched chain alkyl having 1 to 6 carbon atoms (methyl, ethyl, propyl, isopropyl, butyl, pentyl, hexyl etc.). Examples thereof include cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylhexyl, cyclobutylhexyl, cyclopentylhexyl, cyclohexylhexyl, cycloheptylhexyl and the like.

The aralkyl for R or $R^1$ is that wherein the alkyl moiety is alkyl having 1 to 4 carbon atoms, which is exemplified by phenylalkyl such as benzyl, 1-phenylethyl, 2-phenylethyl, 3-phenylpropyl, 4-phenylbutyl and the like.

As the substituents of the cycloalkyl, cycloalkylalkyl, phenyl, aralkyl, each optionally having substituent(s) on the ring, for R or $R^1$, halogen (chlorine, bromine, fluorine, iodine), alkyl (as defined for the alkyl for R and $R^1$), alkoxy (linear or branched chain alkoxy having 1 to 6 carbon atoms, such as methoxy, ethoxy, propoxy, isopropoxy, butoxy, isobutoxy, secondary butoxy, tertiary butoxy, pentyloxy, hexyloxy and the like), aralkyl (as defined for the aralkyl for R and $R^1$), haloalkyl (the alkyl for R and $R^1$, which is substituted by 1 to 5 halogens, such as fluoromethyl, difluoromethyl, trifluoromethyl, 2,2,2-trifluoroethyl, 2,2,3,3,3-pentafluoropropyl and the like), nitro, amino, cyano, azido and the like can be mentioned.

As the heterocyclic group formed by R and $R^1$ in combination, together with the adjacent nitrogen atom, which further optionally contains, in the ring, an oxygen atom, a sulfur atom, or a nitrogen atom optionally having a substituent, a 5- or 6-membered ring and fused rings thereof are preferable. Examples thereof include 1-pyrrolidinyl, piperidino, 1-piperazinyl, morpholino, thiomorpholino, 1-imidazolyl, 2,3-dihydrothiazol-3-yl and the like. As the substituent of the nitrogen atom optionally having a substituent, alkyl, aralkyl, haloalkyl and the like can be mentioned. Here, alkyl, aralkyl and haloalkyl are as defined for R and $R^1$.

The alkyl for $R^2$ is as defined for the alkyl for R and $R^1$.

The halogen, alkyl, alkoxy and aralkyl for $R^3$ or $R^4$ are as defined for R and $R^1$.

The acyl for $R^3$ or R is alkanoyl having 2 to 6 carbon atoms (acetyl, propionyl, butyryl, valeryl, pivaloyl etc.), benzoyl, or phenylalkanoyl wherein the alkanoyl moiety has 2 to 4 carbon atoms (phenylacetyl, phenylpropionyl, phenylbutyryl etc.).

The alkylamino for $R^3$ or $R^4$ is alkylamino wherein the alkyl moiety is linear or branched chain alkyl having 1 to 6 carbon atoms, which is exemplified by methylamino, ethylamino, propylamino, isopropylamino, butylamino, isobutylamino, secondary butylamino, tertiary butylamino, pentylamino, hexylamino and the like.

The acylamino for $R^3$ or $R^4$ is acylamino wherein the acyl moiety is alkanoyl having 2 to 6 carbon atoms, benzoyl, or phenylalkanoyl wherein the alkanoyl moiety has 2 to 4 carbon atoms, and the like, which is exemplified by acetylamino, propionylamino, butyrylamino, valerylamino, pivaloylamino, benzoylamino, phenylacetylamino, phenylpropionylamino, phenylbutyrylamino and the like.

The alkylthio for $R^3$ or $R^4$ is alkylthio wherein the alkyl moiety is linear or branched chain alkyl having 1 to 6 carbon atoms, which is exemplified by methylthio, ethylthio, propylthio, isopropylthio, butylthio, isobutylthio, secondary butylthio, tertiary butylthio, pentylthio, hexylthio and the like.

The aralkyloxy for $R^3$ or $R^4$ is that having aralkyl wherein the alkyl moiety is alkyl having 1 to 4 carbon atoms, which is exemplified by benzyloxy, 1-phenylethyloxy, 2-phenylethyloxy, 3-phenylpropyloxy, 4-phenylbutyloxy and the like.

The aralkylthio for $R^3$ or $R^4$ is that having aralkyl wherein the alkyl moiety is alkyl having 1 to 4 carbon atoms, which is exemplified by benzylthio, 1-phenylethylthio, 2-phenylethylthio, 3-phenylpropylthio, 4-phenylbutylthio and the like.

The alkoxycarbonyl for $R^3$ or $R^4$ is that wherein the alkoxy moiety is linear or branched chain alkoxy having 1 to 6 carbon atoms, which is exemplified by methoxycarbonyl, ethoxycarbonyl, propoxycarbonyl, isopropoxycarbonyl, butoxycarbonyl, isobutoxycarbonyl, secondary butoxycarbonyl, tertiary butoxycarbonyl, pentyloxycarbonyl, hexyloxycarbonyl and the like.

The mono- or di-alkylcarbamoyl for $R^3$ or $R^4$ is carbamoyl mono- or di-substituted by alkyl having 1 to 4 carbon atoms, which is exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

The alkoxy for $R^5$ is as defined for the alkoxy for R and $R^1$.

The alkoxycarbonyloxy for $R^5$ is that wherein the alkoxy moiety is linear or branched chain alkoxy having 1 to 6 carbon atoms, which is exemplified by methoxycarbonyloxy, ethoxycarbonyloxy, propoxycarbonyloxy, isopropoxycarbonyloxy, butoxycarbonyloxy, isobutoxycarbonyloxy, secondary butoxycarbonyloxy, tertiary butoxycarbonyloxy, pentyloxycarbonyloxy, hexyloxycarbonyloxy and the like.

The alkanoyloxy for $R^5$ is that wherein the alkanoyl moiety is alkanoyl having 2 to 6 carbon atoms, which is exemplified by acetyloxy, propionyloxy, butyryloxy, valeryloxy, pivaloyloxy and the like.

The aralkyloxycarbonyloxy for $R^5$ is that wherein the alkyl moiety has aralkyl having alkyl having 1 to 4 carbon atoms, which is exemplified by benzyloxycarbonyloxy, 1-phenylethyloxycarbonyloxy, 2-phenylethyloxycarbonyloxy, 3-phenylpropyloxycarbonyloxy, 4-phenylbutyloxycarbonyloxy and the like.

The alkyl for $R^6$ is as defined for the alkyl for R and $R^1$, the alkyl for $R^8$ or $R^9$ is as defined for the alkyl for R and $R^1$, and the aralkyl for $R^8$ or $R^9$ is as defined for the aralkyl for R and $R^1$.

The alkyl for $R^7$ is as defined for the alkyl for R and $R^1$, and the aralkyl for $R^7$ is as defined for the aralkyl for R and $R^1$.

As the heterocyclic group formed by $R^6$ and $R^7$ in combination, which further optionally contains, in the ring, an oxygen atom, a sulfur atom, or a nitrogen atom optionally having a substituent, imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl, and benzoimidazol-2-yl, benzothiazol-2-yl and benzoxazol-2-yl, each optionally having substituent(s) such as halogen, alkyl, alkoxy, haloalkyl, nitro, amino, phenyl, aralkyl and the like, and the like can be mentioned. Here, halogen, alkyl, alkoxy, haloalkyl and aralkyl are as defined for R and $R^1$.

As the substituent of the above-mentioned nitrogen atom optionally having a substituent, alkyl, aralkyl, haloalkyl and the like can be mentioned. Here, alkyl, aralkyl and haloalkyl are as defined for R and $R^1$.

The hydroxyalkyl for $R^{10}$ or $R^{11}$ is linear or branched chain alkyl having 1 to 6 carbon atoms, which is substituted by 1-3 hydroxy. For example, hydroxymethyl, 2-hydroxyethyl, 1-hydroxyethyl, 3-hydroxypropyl, 4-hydroxybutyl and the like can be mentioned.

The alkyl for $R^{10}$ or $R^{11}$ is as defined for the alkyl for R and $R^1$, the haloalkyl and alkoxycarbonyl for $R^{10}$ or $R^{11}$ is as defined for R and $R^1$, and the aralkyl for $R^{10}$ or $R^{11}$ is as defined for the aralkyl for R and $R^1$.

The cycloalkyl formed by $R^{10}$ and $R^{11}$ in combination is also as defined for the cycloalkyl for R or $R^1$.

The alkyl for L is as defined for the alkyl for R and $R^1$.

The aminoalkyl for L is linear or branched chain alkyl having 1 to 6 carbon atoms, which is substituted by amino and, for example, aminomethyl, 2-aminoethyl, 1-aminoethyl, 3-aminopropyl, 4-aminobutyl, 5-aminopentyl, 6-aminohexyl and the like can be mentioned.

The mono- or di-alkylaminoalkyl for L is aminoalkyl mono- or di-substituted by alkyl having 1 to 4 carbon atoms, which is exemplified by methylaminomethyl, dimethylaminomethyl, ethylaminomethyl, diethylaminomethyl, propylaminomethyl, dipropylaminomethyl, butylaminomethyl, dibutylaminomethyl, 2-dimethylaminoethyl, 2-diethylaminoethyl and the like.

The carbamoylalkyl for L is linear or branched chain alkyl having 1 to 6 carbon atoms, which is substituted by carbamoyl and, for example, carbamoylmethyl, 2-carbamoylethyl, 1-carbamoylethyl, 3-carbamoylpropyl, 4-carbamoylbutyl, 5-carbamoylpentyl, 6-carbamoylhexyl and the like can be mentioned.

The phthalimidoalkyl for L is linear or branched chain alkyl having 1 to 6 carbon atoms, which is substituted by phthalimide and, for example, phthalimidomethyl, 2-phthalimidoethyl, 1-phthalimidoethyl, 3-phthalimidopropyl, 4-phthalimidobutyl, 5-phthalimidopentyl, 6-phthalimidohexyl and the like can be mentioned.

The alkyl for B is as defined for the alkyl for R and $R^1$.
The alkoxy for B is as defined for the alkoxy for R and $R^1$.
The aralkyl for B is as defined for the aralkyl for R and $R^1$.
The aralkyloxy for B is as defined for the aralkyloxy for $R^3$ and $R^4$.
The aminoalkyl for B is as defined for the aminoalkyl for L.
The hydroxyalkyl for B is as defined for the hydroxyalkyl for $R^{10}$ and $R^{11}$.

The alkanoyloxyalkyl for B is linear or branched chain alkyl having 1 to 6 carbon atoms, which is substituted by alkanoyloxy wherein the alkanoyl moiety has 2 to 6 carbon atoms and, for example, acetyloxymethyl, propionyloxymethyl, butyryloxymethyl, valeryloxymethyl, pivaloyloxymethyl, acetyloxyethyl, propionyloxyethyl, butyryloxyethyl, valeryloxyethyl, pivaloyloxyethyl and the like can be mentioned.

The alkoxycarbonylalkyl for B is linear or branched chain alkyl having 1 to 6 carbon atoms, which is substituted by alkoxycarbonyl wherein the alkoxy moiety has 1 to 6 carbon atoms and, for example, methoxycarbonylmethyl, ethoxycarbonylmethyl, propoxycarbonylmethyl, isopropoxycarbonylmethyl, butoxycarbonylmethyl, isobutoxycarbonylmethyl, secondary butoxycarbonylmethyl, tertiary butoxycarbonylmethyl, pentyloxycarbonylmethyl, hexyloxycarbonylmethyl, methoxycarbonylethyl, ethoxycarbonylethyl, propoxycarbonylethyl, isopropoxycarbonylethyl, butoxycarbonylethyl, isobutoxycarbonylethyl, secondary butoxycarbonylethyl, tertiary butoxycarbonylethyl, pentyloxycarbonylethyl, hexyloxycarbonylethyl and the like can be mentioned.

The halogen for $Q^1$, $Q^2$ or $Q^3$ is as defined for the halogen for R and $R^1$. The aralkyloxy for $Q^1$ or $Q^2$ is as defined for the aralkyloxy for $R^3$ and $R^4$.

The alkoxy for $Q^3$ is as defined for the alkoxy for R and $R^1$.

The alkylene for W, X or Y is linear or branched chain alkylene having 1 to 6 carbon atoms, which is exemplified by methylene, ethylene, trimethylene, propylene, tetramethylene, pentamethylene, hexamethylene and the like.

The alkenylene for Y is linear or branched chain alkenylene having 2 to 6 carbon atoms, which is exemplified by vinylene, propenylene, butenylene, pentenylene and the like.

The alkyl for Rb is as defined for the alkyl for R and $R^1$.
The aralkyl for Rb is as defined for the aralkyl for R and $R^1$.
The aminoalkyl for Rb is as defined for the aminoalkyl for L.

The mono- or di-alkylaminoalkyl for Rb is as defined for the mono- or di-alkylaminoalkyl for L.

The nitrogen-containing heterocycle for Rc, when it is a monocycle, is exemplified by pyridine, pyrimidine, pyridazine, triazine, pyrazole and triazole, and when it is a fused ring, is exemplified by pyrrolopyridine (1H-pyrrolo[2,3-b]pyridine, 1H-pyrrolo[3,2-b]pyridine, 1H-pyrrolo[3,4-b]

pyridine etc.), pyrazolopyridine (1H-pyrazolo[3,4-b]pyridine, 1H-pyrazolo[4,3-b]pyridine etc.), imidazopyridine (1H-imidazo[4,5-b]pyridine etc.), pyrrolopyrimidine (1H-pyrrolo[2,3-d]pyrimidine, 1H-pyrrolo[3,2-d]pyrimidine, 1H-pyrrolo[3,4-d]pyrimidine etc.), pyrazolopyrimidine (1H-pyrazolo[3,4-d]pyrimidine, pyrazolo[1,5-a]pyrimidine, 1H-pyrazolo[4,3-d]pyrimidine etc.), imidazopyrimidine (imidazo[1,2-a]pyrimidine, 1H-imidazo[4,5-d]pyrimidine etc.), pyrrolotriazine (pyrrolo[1,2-a]-1,3,5-triazine, pyrrolo[2,1-f]-1,2,4-triazine etc.), pyrazolotriazine (pyrazolo[1,5-a]-1,3,5-triazine etc.), triazolopyridine (1H-1,2,3-triazolo[4,5-b]pyridine etc.), triazolopyrimidine (1,2,4-triazolo[1,5-a]pyrimidine, 1,2,4-triazolo[4,3-a]pyrimidine, 1H-1,2,3-triazolo[4,5-d]pyrimidine etc.), cinnoline, quinazoline, quinoline, pyridopyridazine (pyrido[2,3-c]pyridazine etc.), pyridopyrazine (pyrido[2,3-b]pyrazine etc.), pyridopyrimidine (pyrido[2,3-d]pyrimidine, pyrido[3,2-d]pyrimidine etc.), pyrimidopyrimidine (pyrimido[4,5-d]pyrimidine, pyrimido[5,4-d]pyrimidine etc.), pyrazinopyrimidine (pyrazino[2,3-d]pyrimidine etc.), naphthyridine (1,8-naphthyridine etc.), tetrazolopyrimidine (tetrazolo[1,5-a]pyrimidine etc.), thienopyridine (thieno[2,3-b]pyridine etc.), thienopyrimidine (thieno[2,3-d]pyrimidine etc.), thiazolopyridine (thiazolo[4,5-b]pyridine, thiazolo[5,4-b]pyridine etc.), thiazolopyrimidine (thiazolo[4,5-d]pyrimidine, thiazolo[5,4-d]pyrimidine etc.), oxazolopyridine (oxazolo[4,5-b]pyridine, oxazolo[5,4-b]pyridine etc.), oxazolopyrimidine (oxazolo[4,5-d]pyrimidine, oxazolo[5,4-d]pyrimidine etc.), furopyridine (furo[2,3-b]pyridine, furo[3,2-b]pyridine etc.), furopyrimidine (furo[2,3-d]pyrimidine, furo[3,2-d]pyrimidine etc.), 2,3-dihydropyrrolopyridine (2,3-dihydro-1H-pyrrolo[2,3-b]pyridine, 2,3-dihydro-1H-pyrrolo[3,2-b]pyridine etc.), 2,3-dihydropyrrolopyrimidine (2,3-dihydro-1H-pyrrolo[2,3-d]pyrimidine, 2,3-dihydro-1H-pyrrolo[3,2-d]pyrimidine etc.), 5,6,7,8-tetrahydropyrido[2,3-d]pyrimidine, 5,6,7,8-tetrahydro-1,8-naphthyridine, 5,6,7,8-tetrahydroquinoline and the like, and when these rings are hydrogenated aromatic rings, the carbon atom in the ring may be carbonyl and examples thereof include 2,3-dihydro-2-oxopyrrolopyridine, 2,3-dihydro-2,3-dioxopyrrolopyridine, 7,8-dihydro-7-oxo-1,8-naphthyridine, 5,6,7,8-tetrahydro-7-oxo-1,8-naphthyridine and the like.

These rings are optionally substituted by substituent(s) such as halogen, alkyl, alkoxy, aralkyl, haloalkyl, nitro, amino, alkylamino, cyano, formyl, acyl, aminoalkyl, mono- or di-alkylaminoalkyl, azido, carboxy, alkoxycarbonyl, carbamoyl, mono- or di-alkylcarbamoyl, alkoxyalkyl (methoxymethyl, methoxyethyl, methoxypropyl, ethoxymethyl, ethoxyethyl, ethoxypropyl etc.), hydrazino optionally having substituent(s) and the like.

As the substituent of the hydrazino optionally having substituent(s), alkyl, aralkyl, nitro, cyano and the like can be mentioned, wherein alkyl and aralkyl are as defined for the alkyl and aralkyl for R and R¹. Examples thereof include methylhydrazino, ethylhydrazino, benzylhydrazino and the like.

The compound to be used as the amide compound represented by the formula (I) of the present invention may be a pharmaceutically acceptable acid addition salt, wherein the acid is exemplified by inorganic acids such as hydrochloric acid, hydrobromic acid, sulfuric acid and the like, organic acids such as methanesulfonic acid, fumaric acid, maleic acid, mandelic acid, citric acid, tartaric acid, salicyl acid and the like. The compound having a carboxyl group can be converted to a salt with a metal such as sodium, potassium, calcium, magnesium, aluminum and the like, or a salt with amino acid such as lysine and the like. Furthermore, 1 hydrate, dihydrate, 1/2 hydrate, 1/3 hydrate, 1/4 hydrate, 2/3 hydrate, 3/2 hydrate, 6/5 hydrate and the like thereof are also encompassed in the present invention.

The compound used as the amide compound of the formula (I) of the present invention may be provided as a prodrug. As used herein, the prodrug is a compound that can be converted to the aforementioned amide compound of the formula (I) within living organisms and refers to, for example, a compound represented by the formula (I), wherein a moiety such as a carboxyl group (COOH), a hydroxyl group (OH), an amino group (including $NH_2$, amido), a mercapto group (SH) and the like in a molecule is modified (Development Of Pharmaceutical Products, vol. 7 (Molecule Design) Hirokawa Shoten).

When the amide compound represented by the formula (I) includes an optical isomer, a racemate or a cis-trans isomer thereof, all of these can be used in the present invention. The isomers thereof can be produced by isolation according to a conventional method or using starting materials for each isomer.

The amide compound represented by the formula (I) can be synthesized by the method described in WO95/28387 and the like.

The acid addition salt, hydrate and prodrug can also be produced by conventional methods.

In the present invention, of the compounds used as the amide compound represented by the formula (I), the amide compound represented by the formula (I) wherein Ra is a formula:

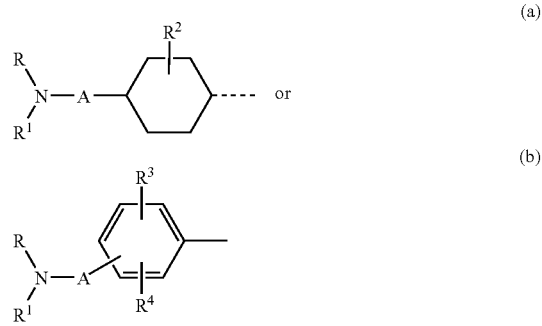

wherein each symbol is as described above (1), is preferable, (R)-(+)-N-(1H-pyrrolo[2,3-b]pyridin-4-yl)-4-(1-aminoethyl)benzamide hydrochloride is more preferable, and (R)-(+)-N-(1H-pyrrolo[2,3-b]pyridin-4-yl)-4-(1-aminoethyl)benzamide 1 hydrochloride is particularly preferable.

The pharmaceutical agent of the present invention recovers the corneal sensitivity that was reduced due to damage or cut or loss of corneal nerve in mammals (e.g., human, monkey, rat, mouse, rabbit, bovine, swine, dog, cat etc.) and birds (e.g., chicken, pigeon, turkey etc.), and is useful as a therapeutic drug capable of improving dry eye symptoms associated with corneal hyposensitivity. For example, it recovers corneal sensitivity function that was reduced by cataract surgery or corneal surgery such as PRK, LASIK, LASEK, keratoplasty surgery and the like, or corneal neurodegenerative diseases such as neuroparalytic keratopathy, corneal ulcer, diabetic keratopathy and the like, and is useful as a therapeutic drug for dry eye associated with corneal hyposensitivity. Moreover, the agent is useful as a therapeutic drug for recovering, in dry eye patients, dry eye conditions and corneal hyposensitivity associated with dry eye.

The pharmaceutical agent of the present invention is systemically or topically administered. Systemically, it is orally administered, and parenterally, it is administered as intravenous injection, subcutaneous injection, intramuscular injection and the like. Topically, it is administered to the eye.

As the dosage form of the pharmaceutical agent of the present invention, solid agents such as powder, granule, tablet, capsule, suppository and the like; liquids such as syrup, injection, ophthalmic solution and the like; and the like can be mentioned. For the production as granules and tablets, any dosage form can be produced by using, for example, excipients (lactose, sucrose, glucose, starch, microcrystalline cellulose and the like), lubricants (magnesium stearate, talc, stearic acid, calcium stearate and the like), disintegrants (starch, carmellose sodium, calcium carbonate and the like), binders (starch paste solution, hydroxypropylcellulose solution, carmellose solution, gum arabic solution, gelatin solution, sodium alginate solution and the like) and the like. For granules and tablets, a coating film may be formed using suitable coating agents (gelatin, sucrose, gum arabic, carnauba wax and the like), enteric coatings (e.g., cellulose acetate phthalate, metacrylic acid copolymer, hydroxypropylmethylcellulose phthalate, carboxymethylethyl and the like) and the like.

For the production as capsule, a mixture of suitable excipients such as magnesium stearate, calcium stearate, talc, light anhydride silicic acid and the like for improving flowability and glidability, microcrystalline cellulose, lactose and the like for flowability under pressurization, as well as the above-mentioned disintegrant and the like added as appropriate is uniformly admixed or granulated or coated granules with a suitable coating agent to form a film and packed in a capsule, or encapsulation-molded with a capsule base having increased plasticity, which contains a suitable capsule base (gelatin and the like), glycerine, mannitol or sorbitol and the like. These capsules may contain coloring agents, preservatives [sulfur dioxide, parabens (methyl paraoxybenzoate, ethyl paraoxybenzoate or propyl paraoxybenzoate)] and the like as necessary. The capsule may be a conventional one, an enteric-coated capsule, a gastric-coated capsule or a release control capsule. When an enteric capsule is produced, a compound coated with an enteric coating agent or a mixture of the compound and the above-mentioned suitable excipients is packed in a conventional capsule or a capsule itself may be coated with an enteric coating agent, or an enteric polymer may be used for molding as a base.

For the production as a suppository, a base for suppository (e.g., cacao butter, macrogol and the like) can be appropriately selected and used.

For the production as a syrup, for example, stabilizers (sodium edetate and the like), suspending agents (gum arabic, carmellose and the like), corrigents (simple syrup, glucose and the like), aromatic and the like can be appropriately selected and used.

For the production of the pharmaceutical agent of the present invention as an injection or ophthalmic solution, it can be produced by dissolving or dispersing the compound in a solution appropriately containing pharmaceutically acceptable additives such as isotonicity agents (sodium chloride, potassium chloride, glycerin, mannitol, sorbitol, boric acid, borax, glucose, propylene glycol and the like), buffers (phosphate buffer, acetate buffer, borate buffer, carbonate buffer, citrate buffer, Tris buffer, glutamate buffer, ε-aminocaproate buffer and the like), preservatives (p-oxybenzoates, chlorobutanol, benzyl alcohol, benzalkonium chloride, sodium dehydroacetate, sodium edetate, boric acid, borax and the like), suspending agents (carboxymethylcellulose sodium, Polysorbate 80, sodium alginate), thickeners (hydroxyethyl cellulose, hydroxypropyl cellulose, polyvinyl alcohol, polyethylene glycol and the like), stabilizers (sodium bisulfite, sodium thiosulfate, sodium edetate, sodium citrate, ascorbic acid, dibutylhydroxytoluene and the like), pH adjusting agents (hydrochloric acid, sodium hydroxide, phosphoric acid, acetic acid and the like), and the like.

While the amount of the additives to be used for the above-mentioned syrup, injection and ophthalmic solution varies depending on the kind of the additives to be used, use and the like, they may be added at a concentration capable of achieving the purpose of the additive, and an isotonicity agent is generally added in about 0.5-about 5.0 w/v % to make the osmotic pressure about 229-about 343 mOsm. In addition, a buffer is added in about 0.01-about 2.0 w/v %, a thickener is added in about 0.01-about 1.0 w/v %, and a stabilizer is added in about 0.001-about 1.0 w/v %. A pH adjusting agent is appropriately added to generally achieve a pH of about 3-about 9, preferably about 4-about 8.

For particular use as an ophthalmic solution, the lower limit of the concentration of the amide compound represented by the formula (I) is adjusted to generally about 0.00001 w/v %, preferably is about 0.00005 w/v % or more preferably is about 0.0001 w/v % and the upper limit is adjusted to about 1 w/v %, preferably is about 0.1 w/v %, more preferably is about 0.05 w/v %, further preferably is about 0.02 w/v %.

The pharmaceutical agent of the present invention has a Rho-kinase inhibitory action, and is considered to promote corneal neuritogenesis mainly by this action. In neurite extension by NGF (nerve growth factor), F-actin is depolymerized by inhibition of Rho-kinase and neuritogenesis is initiated. Then, F-actin is repolymerized in neurite by activated Rac1, and further extends neurite (Negishi M. and Katoh H., J. Biochem., 132, 157-166, 2002). Given such neuritogenesis mechanism, when the Rho-kinase inhibitory action is sustained for a long time, neuritogenesis may be decelerated or inhibited to resist the repolymerization of F-actin.

While the dose and administration period of the pharmaceutical agent of the present invention vary depending on the target disease, symptom, subject of administration, administration method and the like, in consideration of the above-mentioned action and mechanism of the pharmaceutical agent of the present invention, the administration is preferably conducted for a short administration period of not more than 3 days, not more than 5 days, not more than 1 week, not more than 2 weeks and the like. For example, for topical, short-term administration as an agent for recovering corneal sensitivity to the eye of an adult after PRK surgery, an ophthalmic solution containing about 0.01 w/v % of an amide compound represented by the formula (I) is preferably instilled several times a day for up to 2 weeks by about 20-about 50 μL per instillation. Furthermore, for example, for oral short-term administration as an agent for recovering corneal sensitivity to an adult after LASIK surgery, a tablet containing about 10 mg of an amide compound represented by the formula (I) is preferably administered once or twice a day.

However, the pharmaceutical agent of the present invention can be used not only for a short-term administration but also for a long-term administration by adjusting the single dose and administration frequency in one day. Moreover, intermittent administration at day intervals and the like is also possible, and various treatment plans considered to be suitable for the situation are also available.

For example, for a long-term administration as an agent for recovering corneal sensitivity to an adult after LASIK surgery, an ophthalmic solution containing about 0.01 w/v % of an amide compound of the formula (I) is preferably administered 2-8 times a day by about 20-about 50 μL per administration for the first one week, and an ophthalmic solution containing about 0.003 w/v % or 0.001 w/v % thereof is continuously administered 2-4 times a day for 3 weeks to 6 weeks thereafter. As an example of an intermittent treatment method, for administration as an agent for recovering corneal sensitivity to an adult after LASIK surgery, an ophthalmic solution containing about 0.01 w/v % of an amide compound of the formula (I) is instilled several times a day by about 20-about 50 μL per administration consecutively for one week, then the instillation is discontinued for 1 or 2 weeks. After the discontinuation, the administration is resumed under the same conditions and continued for one week, and then the instillation is discontinued again. Such intermittent administration is preferably repeated until the corneal sensitivity is recovered to the normal level.

Note that a method of promoting corneal neuritogenesis, a method of recovering corneal sensitivity, and a method of treating dry eye, using the above-mentioned pharmaceutical agent, are encompassed in the present invention, and a composition for corneal neuritogenesis, recovery of corneal sensitivity or treating dry eye, which contains an amide compound of the formula (I), is also encompassed in the present invention.

EXAMPLES

The present invention is explained in more detail by referring to the following Examples, which are not to be construed as limitative. In the following Examples, compound 1 means (R)-(+)-N-(1H-pyrrolo[2,3-b]pyridin-4-yl)-4-(1-aminoethyl)benzamide 1 hydrochloride. The compound 1 can be prepared according to the method described in Example 9 of WO95/28387.

Experimental Example 1

Promoting Effect on Neuritogenesis in Cultured Rabbit Trigeminal Nerve Cell

Figure 2:
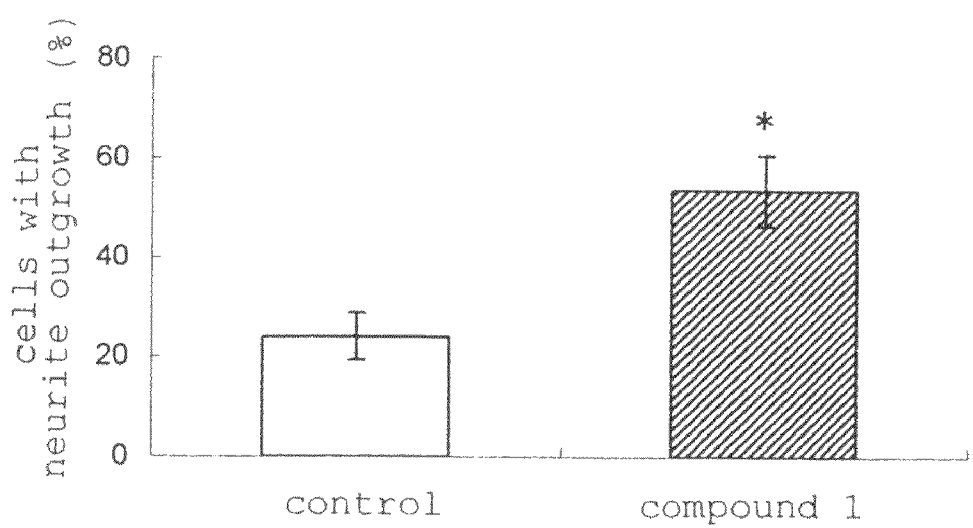
FIG. 2 is a graph showing the proportion of the trigeminal neuritogenetic cell in Experimental Example 1, wherein the vertical axis shows the percentage (%) of neuritogenetic cell to the total cells, each value is a mean±standard deviation of 3 cases, and * shows significance ($p<0.001$) relative to the control group.

1) Animals Used
Japanese White rabbits (2-3 days old) purchased from KITAYAMA LABES Co., Ltd. were used.
2) Test Substance
Compound 1 was used.
3) Test Method
(Cell Culture)
The trigeminal nerve cell was isolated according to the report of Chan et al. (Chan, Kuan Y. and Haschke, Richard H., Exp. Eye Res., 41: 687-699, 1985). To be specific, under ether anesthesia, after cardiac perfusion with saline, the trigeminal ganglia was removed, dispersed using a nerve dispersion solution (SUMITOMO BAKELITE Co., Ltd.) to give a cell suspension. For the cell culture, Neurobasal medium (Invitrogen Corp.) supplemented with B27 Supplement (Invitrogen Corp., final concentration 2% v/v) and L-glutamine (Invitrogen Corp., final concentration 1 mM) was used and the cultured conditions were 5% $CO_2$, 95% air at 37° C. The cells were seeded at about $3 \times 10^3$ cells/well on a cover glass (SUMITOMO BAKELITE) with a polylysine/laminin coating, which was immersed in a 24 well plate. As the test substance, compound 1 (final concentration 1 μM) was added, and the control group was free of addition.
(Immunostaining)
After 48 hr of culture, the cells were fixed with 4% paraformaldehyde at room temperature for 2 hr, and nerve cell body and neurite were fluorescence stained using an anti-neurofilament 200 antibody (Sigma) that specifically recognizes neurofilaments which are intermediate filaments specific to a nerve cell and a fluorescent secondary antibody reactive therewith.
(Image Analysis)
The stained cells were imported as images from a fluorescence microscope into a computer and the cell body diameter and neurite length of the imported cell images were measured using an image analysis software (Image-Pro Plus ver. 4.0, Planetron. Inc.). The cells of 3 wells were measured for each of the compound 1 addition group and the control group. The cells having a neurite with a length of not less than twice the diameter of a cell body were taken as neuritogenetic cells, and the percentage (%) of the neuritogenetic cells in the total cells measured was calculated.
4) Test Results
FIG. 1 shows fluorescence microscope images of cultured rabbit trigeminal nerve cells, wherein A shows the cells of non-addition control group, and B shows the cells of compound 1 addition group. In the non-addition group, not many cells had an extended neurite, but in the compound 1 addition group, many cells having a long-extended neurite were observed. FIG. 2 is a graph showing the proportion of the neuritogenetic cell number in the total number of cells measured. The ratio of the control group and the compound 1 addition group was 24% and 54.6%, respectively, and the compound 1 addition group showed a significantly high neuritogenetic cell percentage relative to the control group (*: $p<0.001$, t-test, N=3, mean±standard deviation).

From the above results, it has been found that compound 1 promotes neuritogenesis of cultured rabbit trigeminal nerve cells.

Experimental Example 2

Improving Effect on Rabbit Corneal Hyposensitivity Using Microkeratome

1) Animals Used
Japanese white rabbits (body weight 2.5-3.0 kg) purchased from Japan SLC were used. The animals were housed separately in cages in a room set to room temperature 23±3° C., humidity 55±10%, 12 hr light cycle (light on 8 am, light off on 8 pm) from arrival to the end of the test. A limited amount of a solid feed (Labo R-stock, Nosan Corporation, 100 g for one day) was given to the animals and a free access to tap water was allowed.
2) Test Substance
As the test substance, compound 1 was used. Compound 1 was dissolved in the following base solution to 0.01% and administered by instillation. The base solution was administered to the control group by instillation.
Base Solution Formulation:

| | |
|---|---|
| sodium dihydrogen phosphate dihydrate | 0.1 g |
| sodium chloride | 0.9 g |
| sodium hydroxide | suitable amount (pH 7) |
| purified water | total amount 100 mL |

3) Test Method
(Selection of Animal and Measurement of Corneal Sensitivity Initial Value)
Prior to the start of the test, the anterior segment of eye of the animal was visually observed and cornea stained marks by fluorescein was observed, and the rabbits showing no abnormality in them were selected. Using Cochet-Bonnet corneal sensitivity meter (manufactured by LUNEAU), the initial value of corneal sensitivity was measured.

(Preparation of Cornea Flap)

Intramuscular injection (0.9 mL/kg) of a Celactal (2% xylazine):Ketalar (5% ketamine)=0.5:1 mixture was given to the animals to perform systemic anesthesia, and the eyeball was sufficiently exposed. Using microkeratome (MK2000, Nidek) attached a rabbit eye adaptor inside a suction ring, a corneal flap (diameter 8.5 mm) was prepared with a 130 μm thick blade (Arbelaez M C. et al., J. Refract Surg., 2002 May-Jun. 18 (3 Suppl): S357-60). The corneal flap was certainly put back into position under a microscope, and the animal was woken up from the anesthesia while observing the animal to prevent displacement of the flap.

(Grouping of Animals)

The next day of the preparation of the corneal flap, the condition of the animals was observed, and the animals having normally positioned corneal flap were selected. These animals were grouped by randomized block design by many variables using SAS preclinical package (Version 5.0, SAS Institute Japan) such that the initial value of the corneal sensitivity before preparation of corneal flap would become uniform.

(Administration)

The test substance solution and the control base solution were administered by instillation for 1 week or 2 weeks from the next day of the corneal flap preparation. The instillation administration was performed to the surgery eye 4 times a day (50 μL one time) at 2 hr intervals using a micropipette. Concurrently, the test substance was instilled 4 times every day for one week after the surgery, 0.1% Bromfenac sodium ophthalmic solution (Bronuck ophthalmic solution, Senju Pharmaceutical Co., Ltd.) was instilled as an anti-inflammatory agent at the first and the third instillations and 0.3% ophthalmic solution of Lomefloxacin hydrochloride (Lomeflon ophthalmic solution, Senju Pharmaceutical Co., Ltd.) was instilled as an antibacterial agent at the second and the fourth instillations.

(Corneal Sensitivity Measurement)

The corneal sensitivity was measured using a Cochet-Bonnet corneal sensitivity meter once every week from one to eight weeks after the surgery. The blind measurement was performed so that the operator would not know which administration group the subject rabbit belonged to.

(Statistical Analysis)

For statistical analysis, a parametric Dunnett multiple comparisons test (one sided) (SAS preclinical package; Version 5.0, SAS Institute Japan) was used and a risk of less than 5% was evaluated as significant.

(Test Results)

Figure 3:
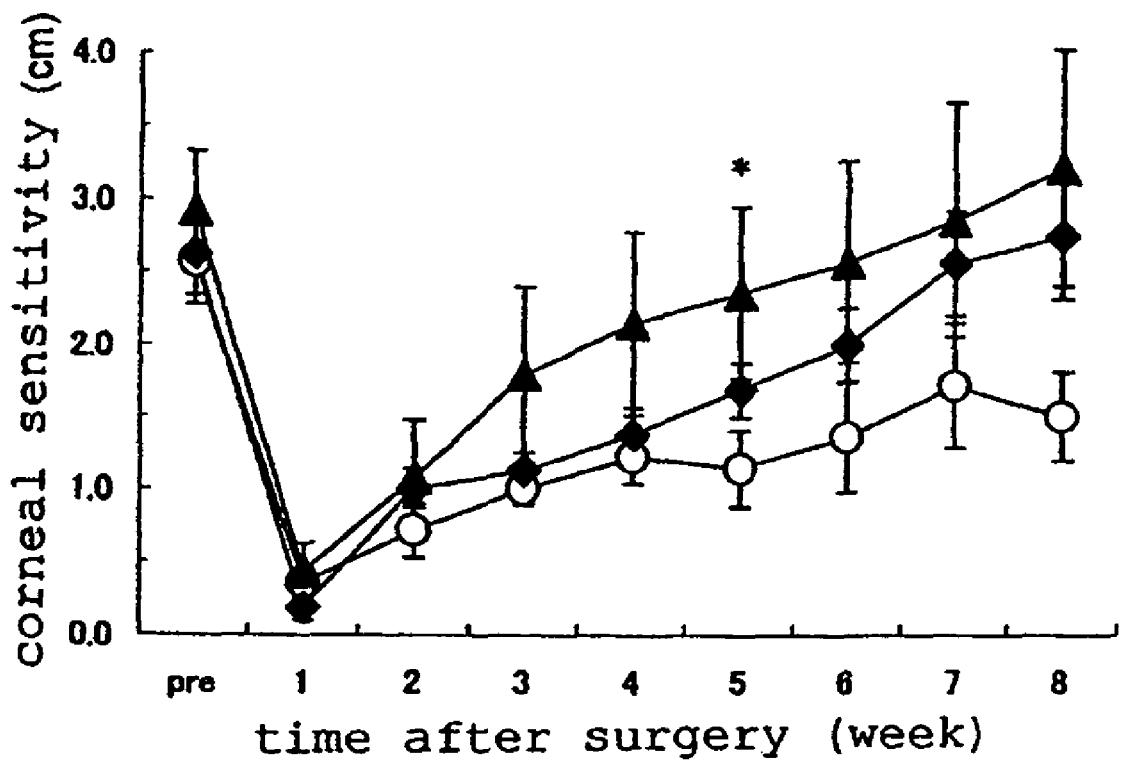
FIG. 3 is the test results of time course changes of rabbit corneal sensitivity in Experimental Example 2, wherein -○- is a control group, -▲- is a test substance one-week administration group, -♦- is a test substance two-week administration group, and * shows significance ($n=7-8$, mean±standard error, *:$p<0.05$) relative to the control group.

FIG. 3 shows time course changes of corneal sensitivity. The corneal sensitivity is expressed by the maximal length of a nylon filament (diameter 0.12 mm) of Cochet-Bonnet corneal sensitivity meter, which induces a brink reflex upon contact of a tip of the filament with the center of the cornea, and the length is shown in the vertical axis of FIG. 3. A rapid reduction of corneal sensitivity was observed in both the base administration group (control group) and the test substance solution administration group at one week postsurgery. Thereafter, the control group showed a gradual recovery of the corneal sensitivity, and the test substance administration group showed better recovery of corneal sensitivity than in the control group. During 2 to 8 postsurgery weeks, the results were fine in the 1-week administration group, the 2-week administration group and the control group in this order. As a result of the statistical analysis, the corneal sensitivity of the 1-week administration group at 5 week postsurgery was significantly high as compared to that of the control group.

In the laser keratomileusis (LASIK), a corneal flap cut using microkeratome is folded back to expose corneal stroma, the cornea stroma is cut by excimer laser irradiation to correct the refraction and the corneal flap is put back in the original position. This test examines the effect of compound 1 on promotion of the recovery of corneal sensitivity using a rabbit corneal hyposensitivity model prepared with this microkeratome. The above test results indicate that compound 1 has an effect of promoting the recovery of corneal hyposensitivity due to corneal nerve section. A possibility has also been suggested that, when the dose is the same, a more effective result may be obtained with a shortened administration time.

Preparation Example 1

Tablet

| | |
|---|---|
| compound 1 | 10 mg |
| lactose | 80 mg |
| starch | 17 mg |
| magnesium stearate | 3 mg |
| microcrystalline cellulose | 10 mg |

Using the above ingredients as materials for one tablet, tablets are formed according to a conventional method. The tablets may be coated as necessary with a conventional enteric coating (e.g., hydroxypropylmethylcellulose phthalate and the like), or a sugar coating or a film (e.g., ethylcellulose). By changing the mixing ratio of additives, tablets containing compound 1 by 20 mg, 5 mg, 1 mg, 0.5 mg, 0.1 mg/tablet (ingredient amount) can be prepared.

Preparation Example 2

Capsule

| | |
|---|---|
| compound 1 | 50 mg |
| mannitol | 75 mg |
| starch | 17 mg |
| calcium stearate | 3 mg |

Using the above ingredients as materials for one capsule, they are uniformly mixed, granulated according to a conventional method and packed in a hard capsule. Before packing, the granules may be coated as necessary with a conventional enteric coating (e.g., hydroxypropylmethylcellulose phthalate), a sugar coating or a film (e.g., ethylcellulose). By changing the mixing ratio of additives, capsules containing compound 1 by 20 mg, 10 mg, 5 mg, 1 mg, 0.5 mg, 0.1 mg/capsule can be prepared.

Preparation Example 3

Injection

| | |
|---|---|
| compound 1 | 750 mg |
| carboxymethylcellulose sodium | 500 mg |
| water for injection | total amount 100 mL |

The above ingredients are aseptically admixed according to a conventional method to give an injection. By changing the mixing ratio of additives, injections containing compound 1 by 1000 mg, 500 mg, 200 mg, 100 mg/100 mL can be prepared.

Preparation Example 4

Ophthalmic Solution

| | |
|---|---|
| compound 1 | 0.005 g |
| boric acid | 0.7 g |
| borax | suitable amount (pH 7) |
| sodium chloride | 0.5 g |
| hydroxymethylcellulose | 0.5 g |
| sodium edetate | 0.05 mg |
| benzalkonium chloride | 0.005 g |
| sterilized purified water | total amount 100 mL |

Sterilized purified water (80 mL) is heated to about 80° C., hydroxymethylcellulose is added and the mixture is stirred until the liquid temperature reaches room temperature. Compound 1, sodium chloride, boric acid, sodium edetate and benzalkonium chloride are added to this solution to allow dissolution. A suitable amount of borax is added to adjust its pH to 7. Sterilized purified water is added to measure up to 100 mL. By changing the mixing ratio of additives, ophthalmic solutions containing compound 1 at 0.1 w/v %, 0.05 w/v %, 0.03 w/v %, 0.01 w/v %, 0.003 w/v % and 0.001 w/v % can be prepared.

Preparation Example 5

Ophthalmic Solution

| | |
|---|---|
| compound 1 | 10 mg |
| D-mannitol | 4.5 g |
| sodium dihydrogen phosphate | 0.1 g |
| sodium hydroxide | suitable amount (pH 7) |
| sterilized purified water | total amount 100 mL |

Compound 1, D-mannitol and sodium dihydrogen phosphate are added to sterilized purified water (80 mL) to allow dissolution. A suitable amount of sodium hydroxide is added to adjust its pH to 7. Sterilized purified water is added to measure up to 100 mL. The prepared ophthalmic solution is aseptically filtered with a membrane filter and filled in a disposable (unit dose) container and sealed. By changing the mixing ratio of additives, ophthalmic solutions containing compound 1 at 0.1 w/v %, 0.05 w/v %, 0.03 w/v %, 0.005 w/v %, 0.003 w/v % and 0.001 w/v % can be prepared.

INDUSTRIAL APPLICABILITY

Since the pharmaceutical agent of the present invention has a corneal neuritogenesis promoting effect, it is useful for improvement of hypofunction of corneal sensitivity due to damaged corneal nerve and the like, as well as improvement of dry eye associated with hypofunction of corneal sensitivity. Specifically, an improving effect on the corneal hyposensitivity after cataract surgery and after PPK, LASIK, LASEK or keratoplasty surgery, corneal hyposensitivity associated with corneal neurodegeneration such as neuroparalytic keratopathy, corneal ulcer, diabetic keratopathy and the like, and dry eye symptoms can be expected.

This application is based on a patent application No. 2004-166445 filed in Japan, the contents of which are hereby incorporated by reference.

The invention claimed is:

1. A method for promoting corneal neuritogenesis, which comprises administering topically to the eye an effective amount of an amide compound represented by the formula (I):

$$Ra-\overset{O}{\underset{}{C}}-\overset{Rb}{\underset{}{N}}-Rc \quad (I)$$

wherein
Ra is a formula:

(a) $R\underset{R^1}{\overset{}{N}}-A-\text{(cyclohexyl with }R^2\text{)}$ (b) $R\underset{R^1}{\overset{}{N}}-A-\text{(phenyl with }R^3, R^4\text{)}$ or (c) $L-N\text{(ring with }R^5\text{)}$ wherein
in the formulas (a) and (b),
R is hydrogen, alkyl, or cycloalkyl, cycloalkylalkyl, phenyl or aralkyl, each optionally having substituent(s) on the ring, or a formula:

(d) $\overset{NR_7}{\underset{R^6}{=}}$ wherein
$R^6$ is hydrogen, alkyl or a formula: $-NR^8R^9$
wherein $R^8$ and $R^9$ are the same or different and each is hydrogen, alkyl, aralkyl or phenyl, and
$R^7$ is hydrogen, alkyl, aralkyl, phenyl, nitro or cyano,
or $R^6$ and $R^7$ in combination form a heterocyclic group further optionally containing, in the ring, an oxygen atom, a sulfur atom, or a nitrogen atom optionally having a substituent,
$R^1$ is hydrogen, alkyl, or cycloalkyl, cycloalkylalkyl, phenyl or aralkyl, each optionally having substituent(s) on the ring,
or R and $R^1$ in combination form, together with the adjacent nitrogen atom, a heterocyclic group further optionally containing, in the ring, an oxygen atom, a sulfur atom, or a nitrogen atom optionally having a substituent, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or di-alkylcarbamoyl or azido, and A is a formula:

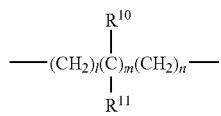

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ in combination form cycloalkyl, and l, m, n are each 0 or an integer of 1-3, and in the formula (c), L is hydrogen, alkyl, aminoalkyl, mono- or di-alkylaminoalkyl, tetrahydrofurfuryl, carbamoylalkyl, phthalimidoalkyl, amidino, or a formula:

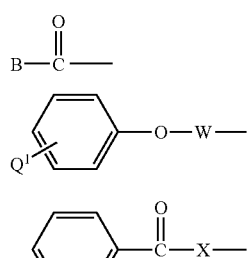

(f)

(g)

(h)

(i)

wherein

B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, a hydroxyl group, aralkyloxy or thienylmethyl, W is alkylene, $Q^2$ is hydrogen, halogen, a hydroxyl group or aralkyloxy, X is alkylene, $Q^3$ is hydrogen, halogen, a hydroxyl group, alkoxy, nitro, amino, 2,3-dihydrofuryl or 5-methyl-3-oxo-2,3,4,5-tetrahydropyridazin-6-yl, and Y is a single bond, alkylene or alkenylene, a bond shown by a broken line and a solid line in the formula (c) is a single bond or a double bond, and $R^5$ is hydrogen, a hydroxyl group, alkoxy, alkoxycarbonyloxy, alkanoyloxy or aralkyloxycarbonyloxy, Rb is hydrogen, alkyl, aralkyl, aminoalkyl or mono- or di-alkylaminoalkyl, and Rc is a nitrogen-containing heterocycle optionally having substituent(s), an isomer thereof and/or a pharmaceutically acceptable acid addition salt thereof, or a prodrug thereof, to a subject in need of promotion of corneal neuritogenesis.

2. The method of claim 1, wherein Ra is a formula:

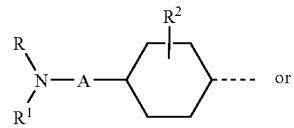

(a)

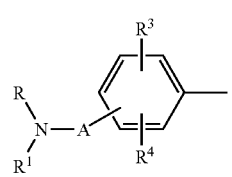

(b)

wherein each symbol is as defined in claim 1.

3. The method of claim 1, wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride.

4. A method for treating dry eye, which comprises administering topically to the eye an effective amount of an amide compound represented by the formula (I):

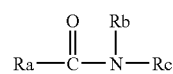

(I)

wherein

Ra is a formula:

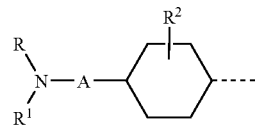

(a)

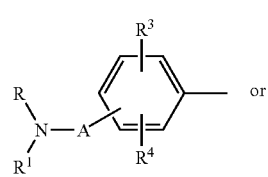

(b)

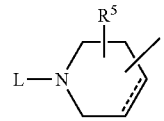

(c)

wherein in the formulas (a) and (b),

R is hydrogen, alkyl, or cycloalkyl, cycloalkylalkyl, phenyl or aralkyl, each optionally having substituent(s) on the ring, or a formula:

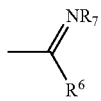

(d)

wherein
R⁶ is hydrogen, alkyl or a formula: —NR⁸R⁹
  wherein R⁸ and R⁹ are the same or different and each is hydrogen, alkyl, aralkyl or phenyl, and
R⁷ is hydrogen, alkyl, aralkyl, phenyl, nitro or cyano,
  or R⁶ and R⁷ in combination form a heterocyclic group further optionally containing, in the ring, an oxygen atom, a sulfur atom, or a nitrogen atom optionally having a substituent,
R¹ is hydrogen, alkyl, or cycloalkyl, cycloalkylalkyl, phenyl or aralkyl, each optionally having substituent(s) on the ring,
or R and R¹ in combination form, together with the adjacent nitrogen atom, a heterocyclic group further optionally containing, in the ring, an oxygen atom, a sulfur atom, or a nitrogen atom optionally having a substituent,
R² is hydrogen or alkyl,
R³ and R⁴ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or di-alkylcarbamoyl or azido, and
A is a formula:

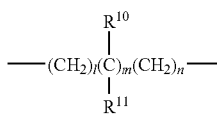

(e)

wherein
R¹⁰ and R¹¹ are the same or different and each is hydrogen, alkyl, haloalkyl, aralkyl, hydroxyalkyl, carboxy or alkoxycarbonyl, or R¹⁰ and R¹¹ in combination form cycloalkyl, and
l, m, n are each 0 or an integer of 1-3, and
in the formula (c),
L is hydrogen, alkyl, aminoalkyl, mono- or di-alkylaminoalkyl, tetrahydrofurfuryl, carbamoylalkyl, phthalimidoalkyl, amidino, or a formula:

(f)

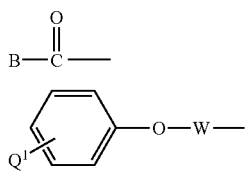

(g)

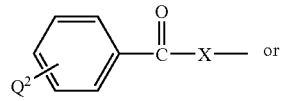

(h)

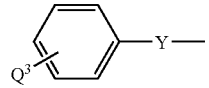

(i)

wherein
B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl,
Q¹ is hydrogen, halogen, a hydroxyl group, aralkyloxy or thienylmethyl,
W is alkylene,
Q² is hydrogen, halogen, a hydroxyl group or aralkyloxy,
X is alkylene,
Q³ is hydrogen, halogen, a hydroxyl group, alkoxy, nitro, amino, 2,3-dihydrofuryl or 5-methyl-3-oxo-2,3,4,5-tetrahydropyridazin-6-yl, and
Y is a single bond, alkylene or alkenylene,
a bond shown by a broken line and a solid line in the formula (c) is a single bond or a double bond, and
R⁵ is hydrogen, a hydroxyl group, alkoxy, alkoxycarbonyloxy, alkanoyloxy or aralkyloxycarbonyloxy,
Rb is hydrogen, alkyl, aralkyl, aminoalkyl or mono- or di-alkylaminoalkyl, and
Rc is a nitrogen-containing heterocycle optionally having substituent(s),
an isomer thereof and/or a pharmaceutically acceptable acid addition salt thereof, or a prodrug thereof, to a subject in need of treatment of dry eye.

5. The method of claim 4, wherein Ra is a formula:

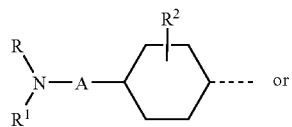

(a)

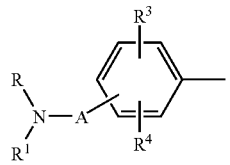

(b)

wherein each symbol is as defined in claim 4.

6. The method of claim 4, wherein the amide compound, an isomer thereof and/or a pharmaceutically acceptable acid addition salt thereof is (R)-(+)-N-(1H-pyrrolo[2,3-b]pyridin-4-yl)-4-(1-aminoethyl)benzamide hydrochloride.

* * * * *